US00PP33457P2

(12) United States Plant Patent
Caudai

(10) Patent No.: US PP33,457 P2
(45) Date of Patent: Sep. 7, 2021

(54) ***ABELIA* PLANT NAMED 'MINCAUTRI'**

(50) Latin Name: *Abelia grandiflora*
Varietal Denomination: MINCAUTRI

(71) Applicant: Hortival Diffusion SAS, Beaufort en Valee (FR)

(72) Inventor: Paolo Caudai, Saint Mathurin sur Loire (IT)

(73) Assignee: Hortival Diffusion SAS

( * ) Notice: Subject to any disclaimer, the term of this patent is extended or adjusted under 35 U.S.C. 154(b) by 0 days.

(21) Appl. No.: 17/038,797

(22) Filed: Sep. 30, 2020

(51) Int. Cl.
*A01H 5/02* (2018.01)
*A01H 6/00* (2018.01)

(52) U.S. Cl.
USPC ..... Plt./226
CPC ..... *A01H 6/00* (2018.05)

(58) Field of Classification Search
USPC ..... Plt./226
CPC ..... A01H 5/02
See application file for complete search history.

*Primary Examiner* — Kent L Bell
(74) *Attorney, Agent, or Firm* — Cassandra Bright

(57) ABSTRACT

A new and distinct *Abelia* cultivar named 'MINCAUTRI' is disclosed, characterized by a stable tri-color foliage of green, cream and pink. In Autumn foliage is has a bright pink hue. Plants are well-branched and of medium size and vigor. Sepals are distinctively variegated green and white, with pink margins in the Autumn. The new variety is an *Abelia*, normally produced as an outdoor garden or container plant.

3 Drawing Sheets

Latin name of the genus and species: *Abelia grandiflora*.
Variety denomination: 'MINCAUTRI'.

BACKGROUND OF THE INVENTION

The new *Abelia* cultivar is a product of chance discovery. The new variety was discovered as a naturally occurring single branch mutation on the parent variety, an unnamed, unpatented *Abelia grandiflora*. The discovery of this new variety was made at a nursery in Pistoia, Italy during July of 2015.

Asexual reproduction of the new cultivar 'MINCAUTRI' was first performed in July of 2015 at a nursery in Pistoia, Italy. Vegetative soft wood cuttings were used. Subsequent propagation has shown that the unique features of this cultivar are stable and reproduced true to type in successive generations.

Date of first sale was Oct. 1, 2019, occurring in France. This sale was made directly by the inventor or one who obtained the claimed invention directly or indirectly from the inventor. This sale and all public disclosures made between Oct. 1, 2019 and the filing of this application fall within the exception allowed under 102(b)(1).

SUMMARY OF THE INVENTION

The cultivar 'MINCAUTRI' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'MINCAUTRI'. These characteristics in combination distinguish 'MINCAUTRI' as a new and distinct *Abelia* cultivar:

1. Stable tri-color foliage, green, cream and pink.
2. Bright pink Autumn color.

3. Medium sized flower colored white.
4. Well branched, rounded plant of medium size.
5. Variegated sepals, green and white, with pink margins in the Autumn.

PARENT COMPARISON

Plants of the new cultivar 'MINCAUTRI' are similar to plants of the seed parent variety in most horticultural characteristics, however, plants of the new cultivar 'MINCAUTRI' differ in the following:

1. The new variety has tri-color foliage parent has solid green foliage.
2. Flowers of the new variety are white, flowers of the parent are white and purple.
3. Plants of the new variety are less vigorous than plants of the parent.
4. Sepals of the new variety are variegated green and white with pink margins in the Autumn, sepals of the parent are red.
4. Plants of the new variety are more upright than the more rounded seed parent.

COMMERCIAL COMPARISON

Plants of the new cultivar 'MINCAUTRI' can be compared to the variety *Abelia* 'Kaleidoscope' U.S. Plant Pat. No. 16,988. These varieties are similar in most horticultural characteristics however, 'MINCAUTRI' differs in the following:

1. Foliage of the new variety is a lighter green, pink and cream, foliage of 'Kaleidoscope' is darker green, yellow, red and orange.
2. Foliage of the new variety is not as glossy as foliage of 'Kaleidoscope'.

BRIEF DESCRIPTION OF THE PHOTOGRAPHS

The accompanying photograph in FIG. 1 illustrates in full color a plant of 'MINCAUTRI' during the Summer grown outdoors, at approximately 2 years old.

Figure 1:
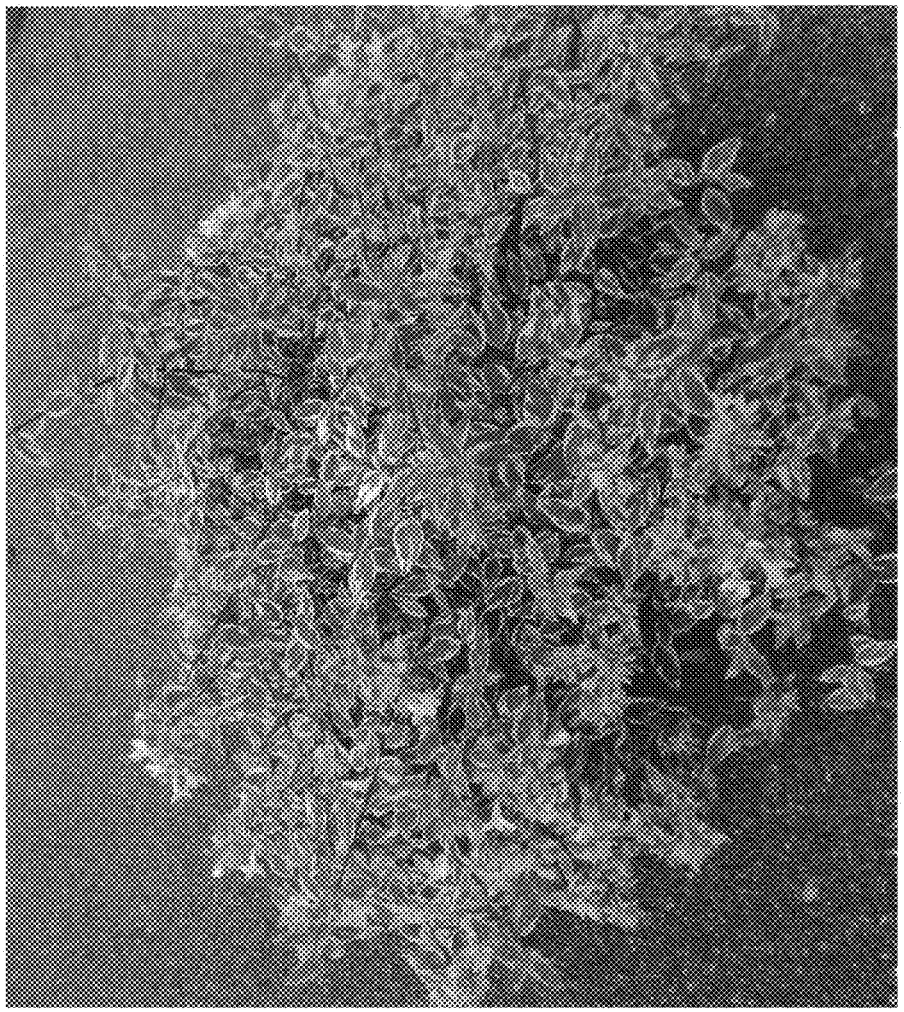
Figure 2:
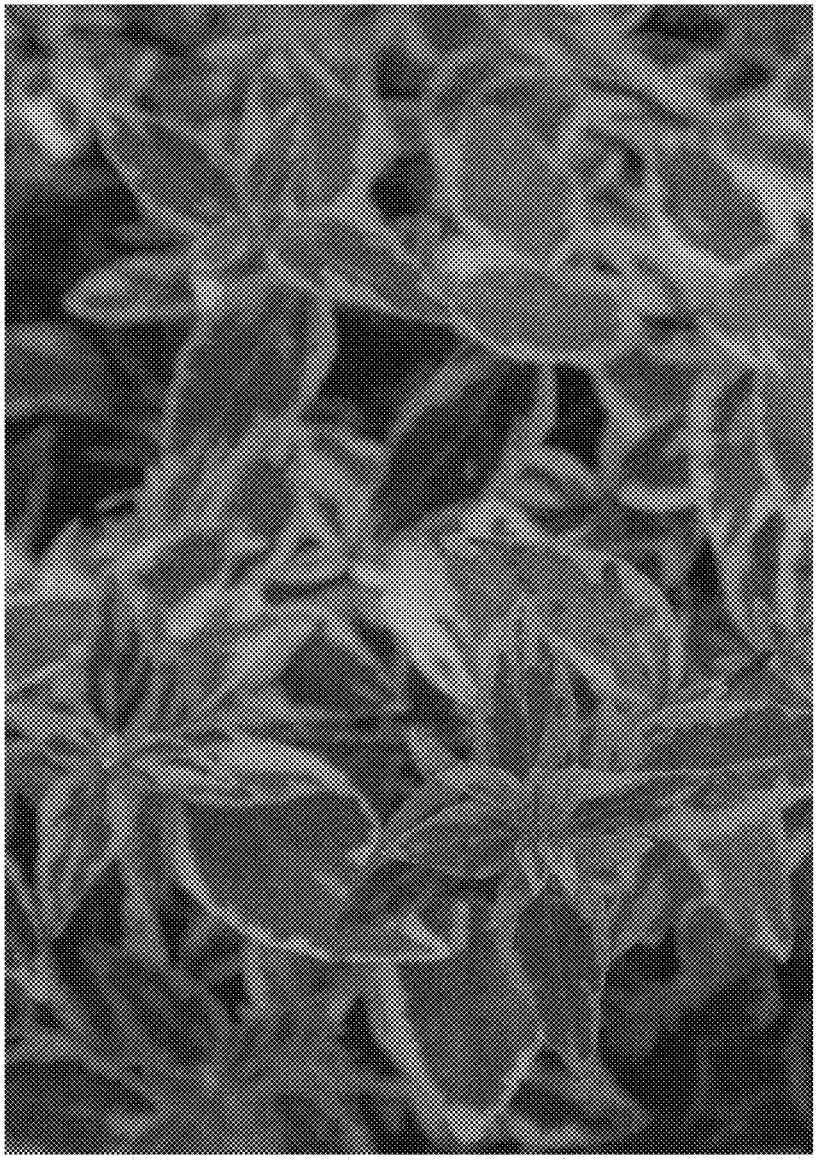
FIG. 2 illustrates a close up view of Fall foliage of 'MINCAUTRI'.
Figure 3:
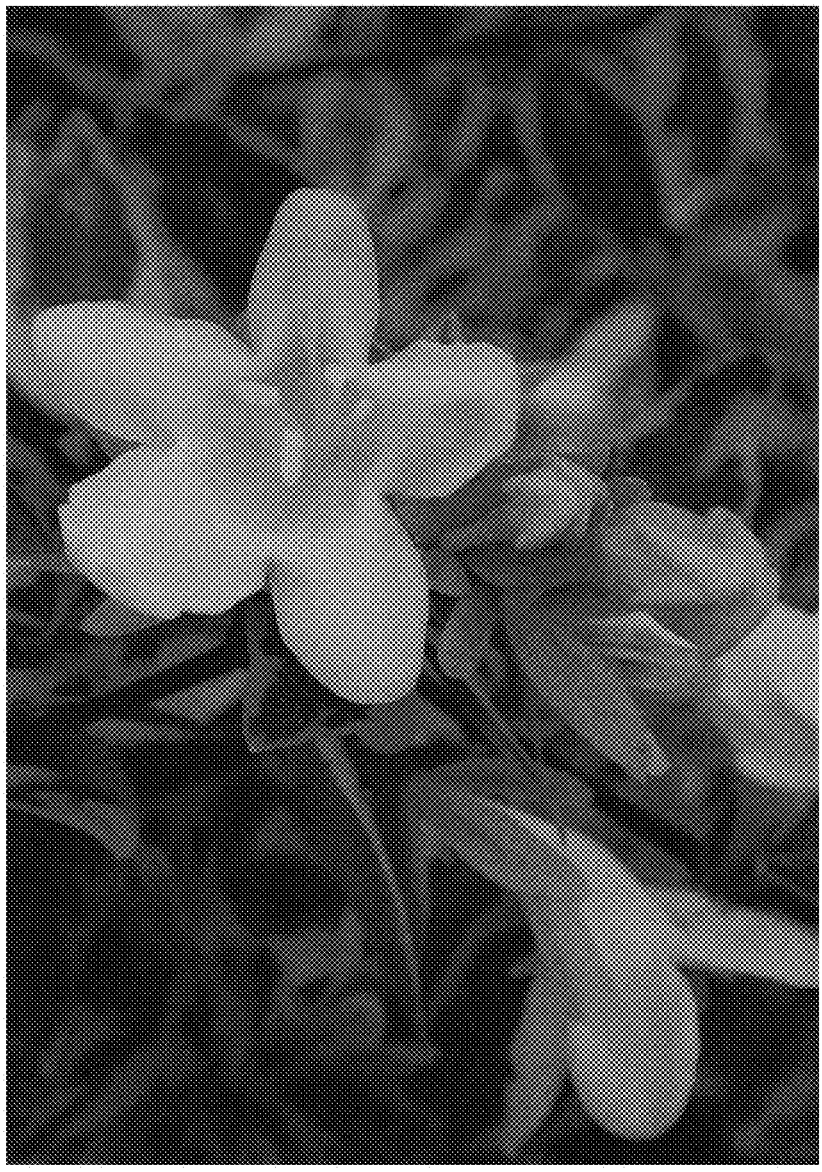
FIG. 3 illustrates a flower late Summer.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, $6^{th}$ edition, except where general terms of ordinary dictionary significance are used. The following observations and measurements describe 'MINCAUTRI' plants grown in a polyhouse in Grand Haven, Mich. Measurements were taken during September of 2020. The plants were about 1.5 years old in 3-gallon containers. The growing temperature ranged from approximately 18° C. to 27° C. during the day and 5° C. to 10° C. at night. Measurements and numerical values represent averages of typical plant types.

Botanical classification: *Abelia grandiflora* 'MINCAUTRI'.

PROPAGATION

Time to initiate roots: 1 to 2 months at approximately 18 to 27° C.

Time to produce a rooted young plant: About 40 days at approximately 18 to 27° C.

PLANT

Plant type: Perennial flowering shrub.

Age of plant described: Approximately 1.5 years old.

Growth habit: Semi-erect, outwardly spreading.

Pot size of plant described: 3-gallon pot.

Overall plant shape: Flattened globular.

Height: 19 cm.

Plant spread: 52 cm.

Plant vigor: Moderate.

Branching characteristics: Basal and lateral branching. Some pinching required.

Length of primary lateral branches: Average 24 cm.

Diameter of lateral branches: 2 mm.

Quantity of lateral branches: Average 25 to 30.

Stem:

- *Stem shape.*—Round.
- *Stem strength.*—Strong and flexible.
- *Color.*—Near Greyed-Purple 187B.
- *Texture.*—Slightly pubescent.
- *Angle of attachment.*—45 to 90 degrees from center of plant.

Internode length: 2 cm on average.

Root description: Fibrous, thin root thickness. Some fleshy roots, also thin. Tan and white in color, not effectively measured with a color chart.

FOLIAGE

Leaf:

- *Arrangement.*—Opposite. Single.
- *Leaf shape.*—Lanceolate.
- *Average length.*—2.75 cm.
- *Average width.*—1.25 cm.
- *Apex.*—Acute to acuminate.
- *Base.*—Obtuse.
- *Margin.*—Entire to slightly crenate.
- *Texture of top surface.*—Waxy.
- *Texture of bottom surface.*—Waxy. Protruding mid-rib.
- *Color.*—Young foliage upper side: Spring and Summer: Near RHS Green 139A with Yellow 11A variegation. Fall color: Near RHS Yellow-Green 147A with close to Red 48B variegation. Young foliage under side: Spring and Summer: Near RHS Green 141C with Red 41A variegation. Fall color: Near RHS Green 141C with Red 53D variegation. Mature foliage upper side: Spring and Summer: Near RHS Green 137B with White 155A variegation. Fall color: Near RHS Green 137B with White 155A variegation. Overall colored Red 51C. Mature foliage under side: Spring and Summer: Near RHS Green 137B with White 155A variegation. Fall color: Near RHS Green 137B with White 155A variegation. Overall colored Red 51C.
- *Venation.*—Pattern: Pinnate. Color upper side: Near RHS Yellow-Green 153D. Color under side: Near RHS Yellow-Green 144D.
- *Petiole.*—Average Length: 3 mm. Diameter: 1.5 mm. Petiole color upper side: Near RHS Red 51A. Petiole color lower side: Near RHS Yellow-Green 144D. Petiole Texture upper side: Smooth. Petiole Texture lower side: Smooth.

FLOWER

Natural flowering season: Summer to Fall.

Flowering form: Single funnelform flowers clustered on flowering stem ends. Flower clusters about 6 to 9 cm in height and about 5 to 8 cm wide.

Quantity of flowers per flowering stem: About 5 to 7. A plant of about 1.5 years produces about 300 to 400 flowers and buds in a season.

Flower:

- *Length.*—2.25 cm.
- *Diameter.*—2.0 cm.
- *Throat diameter.*—6 mm.
- *Throat/tube length.*—1 cm.
- *Throat texture.*—Glabrous.
- *Throat color.*—Near White NN155D.
- *Tube diameter.*—About 4 mm.
- *Tube texture.*—Glabrous.
- *Tube color.*—Near White NN155D.
- *Aspect.*—Outward and downward.
- *Persistence.*—Self-cleaning.
- *Fragrance.*—Light and earthy.
- *Longevity.*—About 7-10 days.

Bud:

- *Shape.*—Spatulate.
- *Length.*—1.75 cm.
- *Diameter.*—6 mm.
- *Color.*—Near RHS Yellow 10C.
- *Texture.*—Glabrous.

Petal:

- *Petal arrangement.*—Single funnelform.
- *Number of petals per flower.*—5.
- *Petal shape.*—Elliptic-Obovate.

*Petal base.*—Fused.
*Margin.*—Entire.
*Tip shape.*—Obtuse.
*Unfused length.*—7.5 mm.
*Unfused width.*—5 mm.
*Texture.*—Upper: Pubescent. Lower: Smooth.
*Appearance.*—Delicate, with slightly matte appearance upper and lower surfaces.

Color:
*When opening.*—Upper surface: Near White NN155D. Lower surface: Near White NN155D.
*Fully opened.*—Upper surface: Near White NN155D. Lower surface: Near White NN155D.
*Fading to.*—Upper surface: Near White NN155D. Lower surface: Near White NN155D.

Sepal:
*Arrangement.*—Whorl.
*Number.*—Average 5.
*Shape.*—Linear to oblanceolate.
*Tip.*—Acute.
*Base.*—Cuneate.
*Margin.*—Entire.
*Length.*—6 mm.
*Width.*—3 mm.
*Texture, upper.*—Glabrous.
*Texture, lower.*—Glabrous.
*Color.*—Mature: Upper surface: Near Green 138B with White NN155A variegation. Margins Red 48B in Fall. Lower surface: Near Green 138B with White NN155A variegation. Margins Red 48B in Fall.

Peduncle:
*Length.*—2 mm.
*Diameter.*—1 mm.
*Color.*—Near Greyed-Purple 183C with some Green 138D.
*Orientation.*—About 45°, or less.
*Strength.*—Good.
*Texture.*—Smooth.

Pedicel: Not present.

REPRODUCTIVE ORGANS

Stamens:
*Number.*—Average 4.
*Filament length.*—1.0 cm.
*Filament color.*—Near RHS White 155D.

Anthers:
*Shape.*—Oblong.
*Length.*—2 mm.
*Color.*—Near RHS White 155D.
*Pollen color.*—Near RHS White 155D.
*Pollen amount.*—Scant.

Pistil:
*Number.*—1.
*Length.*—1.0 cm.
*Style.*—Length: 1.0 cm. Color: Near RHS White 155D.
*Stigma.*—Position: Slightly above anthers. Shape: Orbicular. Color: Near RHS Greyed-Green 197D.
*Ovary color.*—Near Yellow-Green 150D.

OTHER CHARACTERISTICS

Seeds and fruits: Not observed.

Disease/pest resistance: Neither resistance nor susceptibility to normal diseases and pests of *Abelia grandiflora* have been observed.

Temperature tolerance: Typical range USDA zones 5 through 9.

What is claimed is:

1. A new and distinct cultivar of *Abelia* plant named 'MINCAUTRI' as herein illustrated and described.

* * * * *